United States Patent
Bates et al.

[11] Patent Number: 5,741,423
[45] Date of Patent: Apr. 21, 1998

[54] LIQUID-LIQUID EXTRACTION

[76] Inventors: John Bates, Tamarisk House, High Street, Colne, Huntingdon, Cambridgeshire PE17 3ND; John David Edwards, Sylvan Hurst, Tower Hill, Dorking, Surry RH4 2AN, both of United Kingdom

[21] Appl. No.: 793,263
[22] PCT Filed: Aug. 23, 1995
[86] PCT No.: PCT/GB95/02003
   § 371 Date: Apr. 18, 1997
   § 102(e) Date: Apr. 18, 1997
[87] PCT Pub. No.: WO96/05902
   PCT Pub. Date: Feb. 29, 1996

[30] Foreign Application Priority Data

Aug. 23, 1994 [GB] United Kingdom ............ 9417014
Jan. 9, 1995 [GB] United Kingdom ............ 9500321
Feb. 17, 1995 [GB] United Kingdom ............ 9503114

[51] Int. Cl.⁶ .................................. B01D 11/04
[52] U.S. Cl. ............... 210/634; 210/511; 422/101; 436/178
[58] Field of Search ............... 422/101, 102; 436/177, 178; 210/634, 511, 515, 516, 518

[56] References Cited

U.S. PATENT DOCUMENTS

| | | | |
|---|---|---|---|
| 3,767,365 | 10/1973 | Beesley | 23/269 |
| 4,131,549 | 12/1978 | Ferrara | 210/518 |
| 4,200,611 | 4/1980 | Gorman, Jr. et al. | 422/258 |
| 4,203,840 | 5/1980 | Stoeppler | 210/634 |
| 4,364,832 | 12/1982 | Ballies | 210/518 |
| 4,832,851 | 5/1989 | Bowers | 210/518 |
| 4,891,134 | 1/1990 | Vcelka | 210/518 |
| 5,124,041 | 6/1992 | Sheer | 436/178 |
| 5,269,927 | 12/1993 | Fiehler | 210/518 |
| 5,275,731 | 1/1994 | Jahn | 210/518 |
| 5,308,506 | 5/1994 | McEwen | 210/518 |
| 5,423,989 | 6/1995 | Allen | 436/178 |
| 5,464,541 | 11/1995 | Aysta | 436/178 |
| 5,552,325 | 9/1996 | Nochumson | 436/178 |
| 5,632,895 | 5/1997 | Tsukagoshi | 210/518 |

FOREIGN PATENT DOCUMENTS

| | | | |
|---|---|---|---|
| 14 179 | 1/1980 | European Pat. Off. | 210/518 |
| 1 385 483 | 2/1975 | United Kingdom | 422/101 |
| 2 124 102 | 2/1984 | United Kingdom | 422/101 |

*Primary Examiner*—Ernest G. Therkorn
*Attorney, Agent, or Firm*—Fish & Richardson P.C.

[57] ABSTRACT

Method/apparatus for extracting substance from carrier liquid in first container into an immiscible extraction liquid of different density in second container receiving and locating the first. Substance transfers to extraction liquid at liquids admixture in second container aided by flow control and fine division of carrier liquid force supplied into extraction liquid. Separated liquids receive separator member cooperating with second container as physical barrier with only separated extraction and acquired substance at one side. Centrifuging produces three-stage dividing flow of carrier liquid on the second container wall. Moulded parts suit single use in centrifuge.

12 Claims, 2 Drawing Sheets

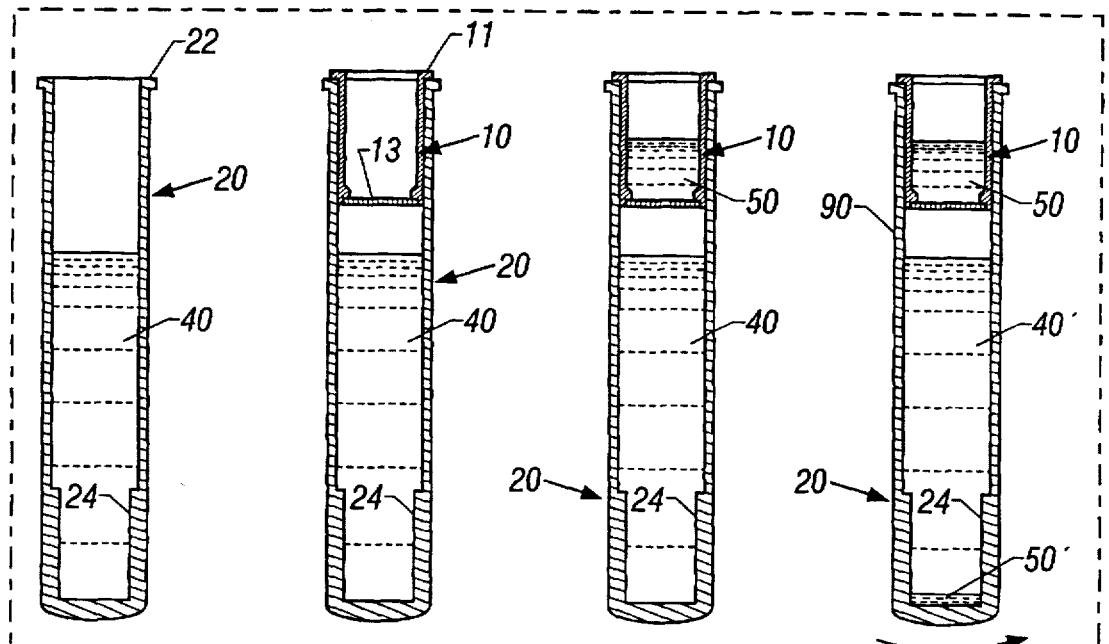
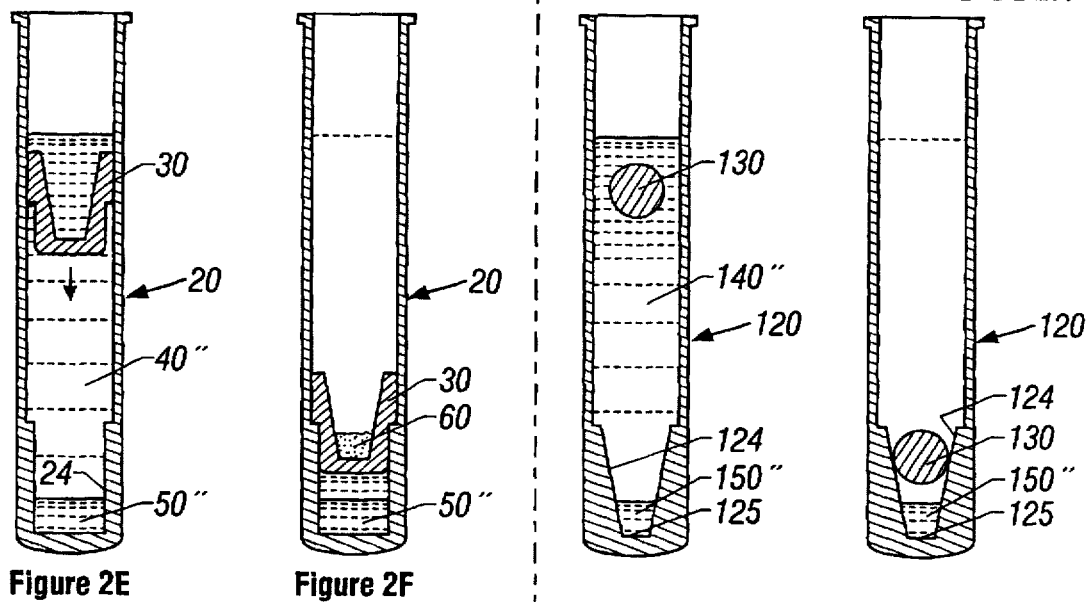
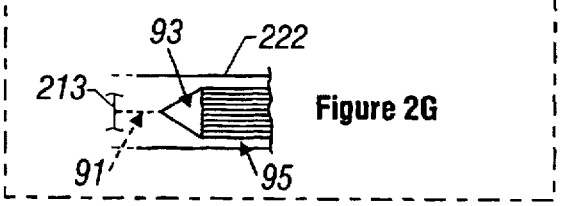
Figure 3

LIQUID-LIQUID EXTRACTION

The invention relates to extracting substances(s) of interest from a first or carrier liquid into a second or extraction liquid, conveniently referred to as liquid-liquid extraction.

Such liquid-liquid extraction is widely used in industry for isolation etc of the substance(s) of interest and/or analysis, purification etc of samples of carrier liquid(s). The procedural steps involved are generally carried out manually. A typical known procedure starts with adding carrier liquid containing substance of interest to a receptacle, often with (or after) desired or necessary adjustments, for example to concentration, pH value, salt content, etc. Extraction liquid immiscible with the carrier liquid and of lower density is then added. The mixture is agitated vigorously by any of a variety of different techniques, for example shaking, vortexing, sonication, etc. During agitation some of the substance of interest passes from the carrier liquid into the extraction liquid, to an extent determined by the so-called partition coefficient of such substance in the conditions concerned. The extraction liquid is then separated from the carrier liquid after a liquid settling step or period leaving the extraction liquid with transferred substance of interest above the denser carrier liquid. Centrifuging of the receptacle is known to speed this settling step. The substance of interest is isolated by drawing off and evaporating the extraction solvent, usually to leave the substance dry.

Commercial laboratories in the pharmaceutical, food, chemical, environmental etc industries may carry out such procedures individually for as many as 50 to 70 samples per person per day. Separate execution of steps required, involving several different physical environments (for liquid dispensing, agitation, centrifuging, evaporation, etc) and considerable rigour of technique required, can be very time-consuming as well as prone to human error.

It is an object of this invention to provide method and means permitting greater regularising of liquid-liquid extraction and leading to reduction of problems and time/plural handling etc associated with prior procedures.

According to one aspect of the invention, there is provided a method of extracting substance of interest from a first or carrier liquid into a second or extraction liquid, said liquids being immiscible and of different densities, said substance transferring from said first liquid to said second liquid at admixture of those liquids, the method comprising admixture and then separation of said liquids in a container followed by insertion into said container of a separator member cooperating with said container as a physical barrier resulting in only separated said second liquid together with said substance as acquired by transfer from said first liquid being at one side of said member.

The first liquid may be denser than the second liquid, and passed through the second liquid herein for transfer of substance(s) of interest and separation of the immiscible liquids. As a result, the less dense separated second liquid will be on top of the first liquid and contain a useful proportion of the substance(s) of interest originally in the first liquid. Further actual physical liquids separation is then by insertion of said member into said container to pass through the separated said second liquid into preferably effectively sealing contact with cooperating internal abutment of said container before reaching the separated said first liquid.

This is generally the case for aqueous-based first or carrier liquids (such as biological fluids, drinks, impure water itself, etc) and second or extraction liquids based on organic solvents (such as ethyl acetate, di-ethyl ether, hexane, etc) for the substance(s) of interest. As is known, suitable solvents can act by preferred solubility for substance(s) of interest that dissolve in water, but are equally applicable to water-insoluble substance(s) of interest carried as an aqueous suspension or homogenate. In principle, of course, the second liquid needs only to have any preferential association for the substance(s) of interest, i.e. not necessarily be a solvent therefor. Moreover, the first liquid need not be aqueous-based.

Indeed, the first or carrier liquid could even be less dense than the second liquid, say with the second or extraction liquid passed through the first or carrier liquid which would then end up complete with transferred content of substance(s) of interest below the first liquid minus substance(s) of interest so far as transferred. The separator member can then be moved through all of the first liquid, preferably also a little of the second liquid; and the one side of the separator member would be its lower rather than its upper side. It could then be advantageous for the second liquid to be accessed by inverting the container and removing a closure, or other communication opened to the container for the separated second liquid.

In any event, it is preferred that admixture of said liquids is by installing the one of lower density in said container followed by applying the other by forcing through flow control means.

According to another or further aspect of the invention, there is provided a method of extracting substance of interest from a first or carrier liquid into a second or extraction liquid, said liquids being immiscible and of different densities, said substance transferring from said first liquid to said second liquid at admixture of those liquids, the method comprising admixture and then separation of said liquids in a container, and including installing the one of lower density in said container followed by applying the other by forcing through flow control means.

Preferably, the other liquid is finely divided by its forcing through said flow control means, typically at least first into small droplets.

According to an apparatus aspect of this invention, there is provided a first container for a or said first or carrier liquid and having an exit with flow control means through which that liquid is finely divided when forced, a second container for receiving a volume of a or said second or extraction liquid and for removably receiving and locating the first container, and a separator member for passage through said second liquid after said first liquid and removal of said first container.

The second container of this apparatus aspect is, of course, equivalent to said container of above method aspects, and reference herein to the former should also be taken as though to the latter where applicable.

Preferred fine division of said other liquid results in droplets or globules or fine streams, whether reaching and passing through said one liquid as so formed at forced supply or breaking out of a possibly intermediate flow along second container walling.

A suitable first container has an exterior formation by which it is removably located in a mouth of said second container. A suitable second container is generally tubular, say with one end blind, and having internally stepped formation of its walling to present a lesser cross-section part for separated said other liquid beyond an open-mouthed part locating the first container that is preferably lipped to fit onto the mouth of the second container, perhaps further preferably with side clearance inside the second container. The separator member may comprise a third container having an exterior formation for its location, preferably sealingly, against a or said internal stepped formation of said second container, preferably with said lesser cross-section part further accommodating the narrower part of the third container above the separated said other liquid.

Preferred flow control means produces low micron or sub-micron division of said other liquid, say as low as 0.01 micron or up to 5 microns, conveniently 0.02 to 2 microns, often about 1 micron or less. Flow resisting microporous material of corresponding pore size is suitable, conveniently at about one millimeter thickness or less, for the flow rate control means, including to produce effective liquid flow rates at low microliter or submicroliter rates per second, say as low as 0.1 microliter or up to 5 microliters, conveniently 1 to 3 microliters, often about 1.5 microliters (as will process 1,000 microliter samples as said other liquid in about 10 minutes. Such microporous material or equivalent provision can be at distal end and/or through side walling of said first container. Resulting high surface areas of force-supplied said other liquid suitably finely divided in passing through said one liquid can substantially assist desired transfer of substance(s) of interest, particularly at indicated flow rates, and taking appropriate account of pore size, thickness, wettability etc of preferred porous material and viscosity, surface tension etc of the liquid concerned. Other feasible forced flow rate control means could employ spray producing means, say compressed gas or mechanically or centrifugal force driven through a fine nozzled head, including by application or adaptation of aerosol-type techniques.

As a particularly significant factor, surface tension of the force-supplied liquid might be adjusted, e.g. reduced by dilution or addition of otherwise benign wetting agent(s) or even just increasing processing temperature. Also, wettability of material of the flow control means, typically said microporous material, by force-supplied liquid contacting it, can differ quite markedly, certainly for such microporous materials as available commercially. Thus, different degrees of fine division, as set by pore size of microporous materials including relative to material thickness, and of wettability can be selected, particularly in relation to surface tension of the force-supplied liquid, in order to optimise practical sample processing times and extraction rates or partition coefficients. Generally, higher wettability leads to finer division, e.g. smaller pore sizes for the same thickness: and surface tension or perhaps greater thickness for greater pore size. Maximum extraction rates or partition coefficients, at least for sample liquids forced by centrifuge action at the above fine division and flow rates into extraction liquids (see further below), can be up to 90% or even higher, at least for depths of liquid to be traversed in the first container approaching 50 or more millimeters, typically about 60 millimeters for quite generally applicable apparatus hereof.

Methods and apparatus of the above aspects of this invention are preferably deployed using a centrifuge with swinging mounts for plural samples serviced together. Then, all or any of requisite force for finely divided supply of said other liquid and for liquids admixing and liquids separation will all be at aided by centrifugal force.

Stroboscopic investigation has been made of preferred centrifuge action with prototype embodiments of this invention using circular cylindrical said first and second containers and a dyed liquid in the second container. At typical applied centrifugal forces of from about 20 G to about 100 G, rotation of the centrifuge appears effectively to limit force-supplied liquid to leaving bottom microporous material of the first container onto the side wall of the second container to a single position at one end of its diameter in the plane of centrifuge rotation that is trailing in the direction of centrifuge rotation. A short orderly line of successive droplets has been observed to spread out into a coalesced smear on the wall of the second container, then to break up into substantially parallel flow lines entering and passing through the liquid in the second container. Such break-up can constitute a two or more times finer division of the force-supplied liquid than the aligned droplets, and can give very high extraction rates or partition coefficients. Sufficient headroom is therefore proposed from the bottom of the second container to liquid level in the first container to accommodate this action, say up to about two centimeters in prototype apparatus. Clearly, both of surface tension of the force-supplied liquid and wettability thereby of the inner wall of the second container can be significant factors, both to such action itself and to related geometries.

Use of a centrifuge in methods hereof can be highly efficient and convenient as two stages of operation. In a first stage, each said second container is installed in said mount provisions and loaded with said volume of said one liquid, and a different said first container is installed in each said second container and loaded with said other liquid. In a second stage, the first containers are removed and a or said separator member installed one in each said second container. The second stage of centrifuge operation can most usefully further involve application of heat and vacuum for evaporation of said other liquid to one side of the separator member as centrifuged into its separating position to leave the associated said substance of interest dry in or on the separator member. The dry substance of interest can then be dissolved in another desired solvent suited to further processing.

It is particularly preferred and advantageous for at least the second containers and separator members, usually also the first containers, to be discardable after a single use.

BRIEF DESCRIPTION OF THE DRAWINGS

Specific implementation for the invention is now described, by way of example, with reference to the accompanying diagrammatic drawings in which:

FIGS. 2A–2G show at (A)–(F) various stages of liquid-liquid extraction using the apparatus of FIG. 1, and at (G) a particular idealised finely dividing liquid flow pattern;

FIG. 3 indicates use of variant apparatus; and

DESCRIPTION OF THE PREFERRED EMBODIMENTS

Figure 1A:
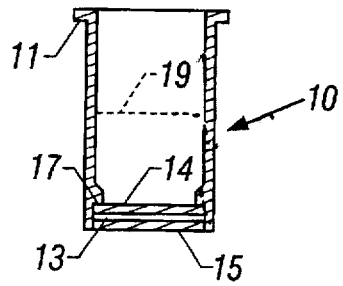
FIGS. 1A, 1B, 1C and 1D show apparatus for use liquid-liquid extraction.
Figure 1D:
Figure 1C:
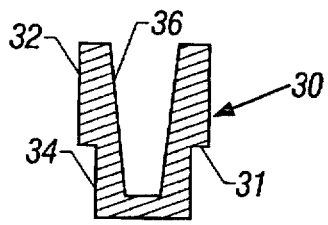
Figure 1B:
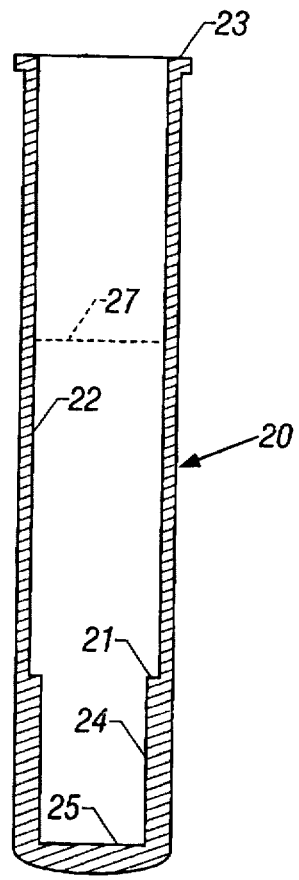

In FIG. 1, there is shown extraction apparatus of one embodiment of the invention. The apparatus comprises first, second and third containers 10, 20 and 30. The first container is a cup-shaped insert 10 (FIG. 1A), the second to receive the insert 10 is a tube 20 with one end blind and the other open (FIG. 1B), and the third also to be received in the second is a cup-shaped separator or barrier plug 30 (FIG. 1C), all of which are made of an appropriate highly economically injection-mouldable solvent-resistant material such as polypropylene. The separator plug 30 is externally stepped at 31 to present exteriorly wider and reduced upper and lower portions 32 and 34, respectively. The step 31 will fit snugly, preferably substantially sealingly, to a medial internal stepping 21 of the second container tube 20 defining an upper or outer part 22 from its mouth 23 wider than an inner or lower part 24 of reduced cross-section to its blind end or bottom 25. Though omitted from specific indication in FIGS. 2A–2F, the separator plug 30 typically has small but sufficient clearances between its exteriorly larger and smaller section portions 32 and 34 and the internally larger and smaller width parts 22 and 24 of the second container tube 20, respectively. Such clearances need not be nominally more than moulding tolerances dictate as minimum for centrifuge-aided passage of the separator plug 30 through extraction liquid in the second container 20. Either or both of the parts 32 and 34 could, of course, be longitudinally grooved as or further to aid passage of extraction liquid. Internally, the separator plug 30 is shown with preferred convergent side walling 36. Moreover, its bottom may incorporate or even be closed off by a relatively dense slug (not shown), say of metal, to assist preferred centrifuging down the second container 20 and getting/maintaining a good seal between the steppings 21, 31. Indeed, such seal may be further enhanced by a specific sealing ring, or formation such as undercutting to leave a thinned, even sharp edged, outer or medial ridge, in either case conveniently with enough give to seal even if preferred centrifuging is in an attitude short of horizontal and there is a consequent tendency for the separator member 30 to tilt slightly.

The insert 10 is adapted by external mouth flanging 11 to fit removably in and be located at the mouth of the second container tube 20 with flanging 11 over the open end or mouth 23 of the tube 20. The insert 10, at least if transparent, may usefully carry marking 19 to indicate a prescribed volume for a sample of carrier liquid from which substance (s) of interest are to be extracted. A permitted volume of up to 1,000 microliters is presently seen as suiting industry requirements and having wide application.

The bottom of the insert 10 has a micro-porous membrane 13, conveniently made of open-pore expanded nylon or polypropylene, which will have a suitable thickness, usually a practical minimum, generally less than 1 mm, say about 0.2 mm; and nominal pore size usually within the range 0.01 micron to 5 microns, typically below 1 micron for 0.2 mm thickness. The membrane 13 is rendered form-sustaining, protected, and held in place in a sandwich structure between two stiff retainers 13 and 14 typically in the form of perforate discs conveniently of polypropylene with suitable apertures for desired liquid flow into and out of the porous membrane 13, typically about 0.5 mm in diameter and about ten per disc. The sandwich structure 13, 14, 15 is shown suitably securely fitted to an end rebate 17 of the insert 10. The tube 20, at least if transparent, may conveniently carry marking 27 to indicate a prescribed volume for an extraction liquid. Whilst not necessarily more than will take up maximum expected substance(s) of interest at desired achievable extraction rates or partition coefficients, such prescribed volume will typically be much greater, being determined in practice by the desired or required length of passage of force-supplied liquid from the insert 10 and convenient dimensions of that insert. A suitable depth, thus length of passage, having wide application is seen as about 50 millimeters or more, conveniently about 60 millimeters.

For various aqueous-based fist or carrier liquids suitable (including as to wettability) open-pore expanded plastics materials for the microporous membranes 13 include a Nylon with nominal pore sizes of 0.2 micron or 0.45 micron as available from Whatman Limited of U.K, and proprietary Supor with nominal pore sizes of 0.2 micron or 0.45 micron or 0.8 micron as available from Gelman Sciences Inc of U.S.A.

A preferred and advantageous extraction method or procedure for carrier liquid samples denser than extraction liquid, and using the apparatus of FIG. 1, can be carried out as follows, see FIG. 2:

(A) A prescribed volume of an extraction liquid 40, typically an organic solvent (e.g. di-ethyl ether) for a sample having an aqueous-based carrier liquid, is dispensed into the tube 20.

(B) The insert 10 is then removably fitted in and to the top of the tube 20 at its mouth 22, located by flanging 11.

(C) A prescribed volume of denser carrier liquid, typically aqueous-based liquid sample 50, with substance of interest and to be extracted is dispensed into the insert 10.

(D) The tube 20 with the insert 10 is centrifuged to force the liquid sample 50 out through the porous membrane 23 in finely divided form and aid its passage into and through the organic solvent (see further below). The latter is now referenced 40' to indicate it taking up substance of interest, thus with a higher level as sample carrier liquid 50' enters it on its way to coalescing and collecting 50' at the bottom of the narrower part 24 of the tube 20.

(E) When all the sample 42 has passed out of the insert 20 and through the organic solvent 40 and collected in a separated volume 50" at the bottom of the tube 20, the insert 10 is removed and the plug 30 is put into the tube 20. The tube 20 with the plug 30 is then centrifuged again to send the plug 30 down the tube 20 and through the extraction liquid towards arresting engagement of the plug step 31 with the tube step 22. The level of liquids in the tube 20 will obviously rise further as shown to accommodate all of the sample liquid 50 and the plug 30.

(F) Such arresting engagement of step 31 with step 21 will be with all the more dense carrier liquid 50", now depleted of at least a useful proportion (which might sometimes be low, say 10%, but can often be much higher, say up to 95%) of the substance of interest originally in the carrier liquid 50. Preferably there will be a safety margin below the plug 30 leaving most (but not quite all) of the organic solvent 40", now containing such extracted substance of interest as it has been able to extract, above the plug 30. It is particularly advantageous to use a centrifuge with vacuum and heat application facilities, and to use them after such arresting engagement, preferably with substantial sealing between steps 21 and 31, to evaporate the organic solvent 40 and leave substance(s) of interest isolated dry (see 60) in the cup-shaped plug 30 ready for redissolving for analysis. Preferred evaporation as part of a two-stage use of a centrifuge is indicated in FIG. 2 at (F) by only dashed extraction liquid level.

It will be appreciated that the volume of the narrower inner or lower part 24 of the second container tube 20 should be at least the sum of the volume of sample 50 and the displacement volume of the lower portion 34 of the separator plug 30 below its step 31, preferably somewhat more as said safety margin.

In connection with using a centrifuge, normally with accommodation for plural apparatus of FIG. 1, it is also to be appreciated that loading of the second container 20 with extraction liquid and/or the first container 10 with sample carrier liquid containing substance(s) of interest can be done in the centrifuge or could precede installing the second container 20 into the centrifuge and/or the first container 10 into the second container 20, even that the second containers 20 could be loaded and associated with loaded or still to be loaded first containers 10 outside the centrifuge.

Also, separator members other than cup-shaped as shown at 30 could be used, whether a simple plug or some other practical configuration. FIG. 3 shows use of a simple spherical member 130 relative to a second container 120 having an inner or lower part 124 that is convergent towards its blind end 125, i.e. rather than simply seating on internal stepping. Evaporation dried out substance(s) of interest would still be readily redissolved from above the separator ball 130.

It will be noted that configuration of each of the component parts (10, 20, 30; 120, 130) lends itself readily to manufacture by high-speed injection moulding, i.e. very economically; and so be suitable for single usage, i.e. discarding after one use.

If the extraction liquid was denser than the carrier liquid, the carrier liquid could be loaded into an as necessarily differently proportioned second container (20, 120) with the extraction liquid into an also if necessarily differently proportioned first container (10, 110) and forced out finely divided to settled through and be separated below the carrier liquid. A suitable separator member, not cup-shaped as for 30, would then go through lighter carrier liquid and slightly into the denser extraction liquid before being arrested, and the extracted substance of interest would require access from below the separator member, say by inverting the second container and removing a blind end cap, or otherwise opening convenient communication with the narrower part (24, 124) of the second container (20, 120).

Figure 4:
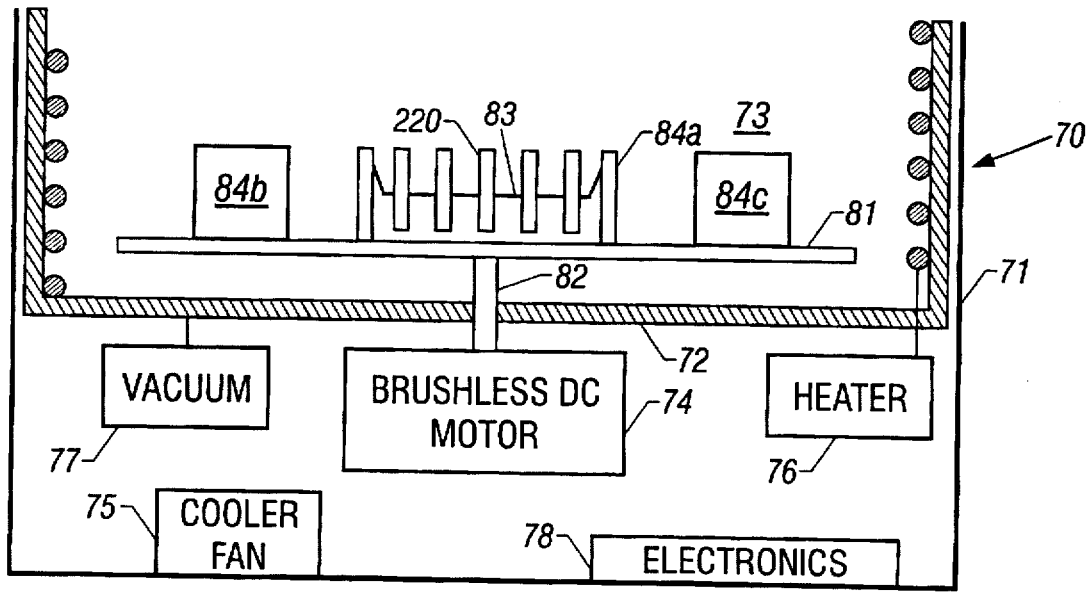
FIG. 4 is an outline sectional view through the lower part of a centrifuge for liquid-liquid extraction as in FIGS. 2 and 3.

Turning to FIG. 4, one suitable centrifuge 70 has a lower part (top not shown) with on outer casing 71 about an inner vacuum case 72 of working chamber 73 shown above drive motor 74, cooler fan 75, heater 76, vacuum drawing 77, and control electronics 78. Within the working chamber 73, a turntable 81 is rotatable by motor drive shaft 82 and shown with common mountings for a balanced or symmetrical array of banks of sample tubes 220 (or holders therefor) along sides of a square, each bank capable of swinging together on swing plates (see 83) extending between end supports (see 84A, 84B, 84C) in which they are journalled.

Stroboscopic investigation has shown that sample liquid centrifugally forced from the first containers (10, 110) goes substantially only from positions at rotationally trailing ends of bottom diameters in the plane of rotation, see position 90 and centrifuge rotation arrow 100 in FIG. 2(D), as an orderly sequence of droplets or globules onto sides of the corresponding second containers (20, 220) to flow therealong aligned for a short distance before spreading into a generally triangular seemingly coalesced smears that each break up into numerous substantially parallel streams entrant the extraction liquid in those second containers (20, 220). These three stages 91, 93 and 95 are shown at (G) in FIG. 2 from microporous membrane fragment 213 onto inner second container tube wall fragment 222 before reaching the extraction liquid, and are found significantly to enhance extraction rates or partition coefficients. Accordingly, adequate headroom will be provided in the second containers between corresponding first containers and the extraction liquid sufficient for such side wall flow, say up to about 2 centimeters. Moreover, further collection followed by break off into streams was noted at the step to part 24 of the first container. High achievable extraction rates up to 90% and more indicate that such stepping is acceptable, even may be beneficial. Also, stroboscopic investigation further indicated likely benefit from operating at temperatures above usual ambient, say up to about 40° C. Thus, using dyed test force-supplied liquid, a band of fuzziness showed up in the extraction liquid parallel with the side wall streams therethrough of the test liquid, which appears to be associated with extraction liquid currents enhancable by convection induced by heating due to raising temperature of operation.

From another point of view, this leads to seeing practicality, even potential advantage, in first containers with stepping down in a T-configuration to give clearance to walls of the second containers and side exit therefrom at least additionally if not wholly alternatively to end exit as above described. It is even feasible that only localised fine-dividing exit provision be made in the first containers, say at a bottom corner or in a bottom radial slot or in a longitudinal side slot, at least if there are mutual location provisions or formations of the first and second containers and of the second containers and the centrifuge mounts therefor.

Methods and apparatus hereof have application in a diverse range of industrial analytical applications, basically from regularising and simplifying the sample extraction process, even the one-trip nature of preferred apparatus. This will apply to the analysis of liquids with substances of interest in solution in particular, but also to the analysis of suspensions of solids as suspensions in liquids and to homogenates. There will be general relevance not only to the pharmaceutical, food, chemical and environmental industries, but also have application in the pathology laboratories and medical/hospital toxicology etc departments. Thus, by allowing rapid extraction from plasma or urine samples in cases of drug overdose, it will allow analysis of the substance overdosed and facilitate taking corrective therapeutic steps.

The sheer number of relevant parameters (e.g. sample surface tension, including possible adjustment thereof; type and thickness of available microporous material; pore size; wetting characteristics, also including adjustment thereof; desired or acceptable or achievable flow rates and/or partition coefficients; processing temperature; centrifuge speed and generated centrifugal force; etc) makes it possible to devise maximum or optimum methodology and apparatus variants for a very wide range of expected applications to various carrier liquids and substances of interest and extraction liquids.

We claim:

1. An apparatus for extracting a substance from a first, carrier liquid using a second, extraction liquid, comprising:
   (a) a first container for holding a first liquid, said first container comprising an exit having a fluid dispersion device which is capable of finely dividing the first liquid;
   (b) a second container for holding a second liquid, said second container being capable of removably receiving the first container; and
   (c) a separator member which is capable of being removably received within said second container and which separates the second container into an upper portion and a lower portion.

2. The extraction apparatus as claimed in claim 1, wherein the second container further comprises an internal abutment for cooperation with the separator member.

3. The extraction apparatus as claimed in claim 1, wherein the lower portion of the second container has a diameter smaller than the diameter of the upper portion of the second container and the separator member cooperates with an internal wall of the container.

4. The extraction apparatus as claimed in claim 1, wherein the separator member has an upper portion which is cup-shaped and open to the upper portion of the container.

5. The extraction apparatus as claimed in claim 1 wherein the first container has flow control means for controlling the supply of the first liquid into the second container.

6. The apparatus according to claim 1 wherein the fluid dispersion device includes one or more apertures adapted to supply the first liquid in droplet form into the second container.

7. A method for extracting a substance from a first, carrier liquid into a second, extraction liquid, said first and second liquids being immiscible and having different densities, the method comprising:
 (a) finely dividing a first liquid containing the substance and introducing the finely divided first liquid into a second liquid;
 (b) admixing the first and second liquids so as to transfer at least a portion of the substance from the first liquid to the second liquid; and
 (c) separating the first liquid from the second liquid, wherein (c) includes introducing a separator member between the first and second liquids such that only the second liquid is on one side of the separator member.

8. The method as claimed in claim 7, further comprising forming a seal between the separator member and the container.

9. The method as claimed in claim 7, wherein the second liquid has a lower density the first liquid.

10. The method as claimed in claim 7, characterized by the further step of removal of second liquid.

11. A method for extracting a substance from a first, carrier liquid using a second, extraction liquid, said first and second liquids being immiscible and of different densities, the method comprising
 (a) providing a first liquid containing the substance, a second liquid and a fluid delivery device between the first and second liquids,
 (b) introducing the first liquid into the second liquid through the fluid delivery device, admixing and separating the first and second liquids such that at least a portion of the substance is transferred from the first liquid to the second liquid during admixture thereof; and
 (c) introducing a separator member between the first and second liquids such that only the second liquid is located on said one side of said member.

12. The method according to claim 11 wherein the fluid delivery device provides the control delivery of the first fluid in droplet form into the second container.

* * * * *